(12) United States Patent
Farhadiroushan et al.

(10) Patent No.: US 9,810,809 B2
(45) Date of Patent: Nov. 7, 2017

(54) METHOD AND SYSTEM FOR DETERMINING DOWNHOLE OPTICAL FIBER ORIENTATION AND/OR LOCATION

(71) Applicant: SILIXA LTD., Elstree Hertfordshire (GB)

(72) Inventors: Mahmoud Farhadiroushan, Elstree Hertfordshire (GB); Tom Parker, Elstree Hertfordshire (GB)

(73) Assignee: SILIXA LTD., Elstree Hertfordshire (GB)

( * ) Notice: Subject to any disclaimer, the term of this patent is extended or adjusted under 35 U.S.C. 154(b) by 0 days.

(21) Appl. No.: 15/114,496

(22) PCT Filed: Jan. 30, 2015

(86) PCT No.: PCT/GB2015/050242
§ 371 (c)(1),
(2) Date: Jul. 27, 2016

(87) PCT Pub. No.: WO2015/114367
PCT Pub. Date: Aug. 6, 2015

(65) Prior Publication Data
US 2016/0349403 A1    Dec. 1, 2016

(30) Foreign Application Priority Data

Jan. 31, 2014  (GB) .................................. 1401671.1
May 16, 2014  (GB) .................................. 1408760.5
Oct. 29, 2014  (GB) .................................. 1419263.7

(51) Int. Cl.
*G01N 21/00*    (2006.01)
*G01V 11/00*    (2006.01)
(Continued)

(52) U.S. Cl.
CPC ........... *G01V 11/005* (2013.01); *G01N 21/64* (2013.01); *G01N 21/68* (2013.01)

(58) Field of Classification Search
CPC ... H01J 37/32935; G01N 21/64; G01N 21/68; G01N 2015/1037; G01J 3/02
(Continued)

(56) References Cited

U.S. PATENT DOCUMENTS 3,668,927 A    6/1972  Howell et al.
3,892,128 A    7/1975  Smith, Jr.
(Continued)

FOREIGN PATENT DOCUMENTS

GB    952813 A      3/1964
GB    2387908 A    10/2003
(Continued)

OTHER PUBLICATIONS

International Searching Authority, International Search Report and Written Opinion for PCT Application No. PCT/GB2015/050242, mailed Sep. 2, 2015.
(Continued)

*Primary Examiner* — Tarifur Chowdhury
*Assistant Examiner* — Md M Rahman
(74) *Attorney, Agent, or Firm* — Honigman Miller Schwartz and Cohn LLP

(57) ABSTRACT

A probe is provided that contacts the inner surface of the casing or other production tubing and imparts energy to the surface at the contact point, for example as heat energy or mechanical energy. Energy is imparted around the circumference of the casing, and a fiber optic distributed sensor located on the outer surface of the casing is used to measure and record the energy that it receives whilst the probe is moved to impart energy around the circumference. A record of energy versus position of the probe around the circum-
(Continued)

ference can be obtained, from which maxima in the detected energy measurements can then be found. The position around the circumference which gave the maximum measurement should be the position at which the optical fiber of the fiber optic distributed sensor is located. In addition, an ultrasonic arrangement is also described, that relies on ultrasonic sound to provide detection.

18 Claims, 15 Drawing Sheets

(51) Int. Cl.
  *G01N 21/68* (2006.01)
  *G01N 21/64* (2006.01)
(58) Field of Classification Search
  USPC .......................................................... 356/72
  See application file for complete search history.

(56) References Cited

U.S. PATENT DOCUMENTS

| | | | |
|---|---|---|---|
| 3,981,187 A | 9/1976 | Howell | |
| 4,855,912 A | 8/1989 | Banavar et al. | |
| 2003/0205428 A1 | 11/2003 | Chang | |
| 2008/0110691 A1 | 5/2008 | Chang et al. | |
| 2008/0149416 A1 | 6/2008 | Coates et al. | |
| 2008/0317095 A1* | 12/2008 | Hadley | E21B 36/04 374/137 |
| 2009/0211756 A1* | 8/2009 | Goodwin | E21B 33/127 166/264 |
| 2009/0314077 A1* | 12/2009 | Tustin | E21B 49/10 73/152.24 |
| 2010/0044103 A1* | 2/2010 | Moxley | E21B 7/14 175/16 |
| 2012/0158307 A1* | 6/2012 | Jay | E21B 47/065 702/11 |
| 2013/0021615 A1 | 1/2013 | Duncan et al. | |
| 2013/0114777 A1* | 5/2013 | Goszczynski | G21C 17/112 376/247 |
| 2013/0329522 A1 | 12/2013 | Skinner et al. | |
| 2015/0013975 A1* | 1/2015 | McColpin | E21B 47/123 166/255.1 |
| 2016/0186554 A1* | 6/2016 | Burgos | E21B 41/0035 166/250.01 |

FOREIGN PATENT DOCUMENTS

| | | |
|---|---|---|
| GB | 2420135 A | 5/2006 |
| GB | 2491658 A | 12/2012 |
| JP | S63165790 A | 7/1988 |
| WO | WO-2004094786 A1 | 11/2004 |
| WO | WO-2010136809 A2 | 12/2010 |
| WO | WO-2012068558 A1 | 5/2012 |
| WO | WO-2012084997 A2 | 6/2012 |
| WO | WO-2013030555 A2 | 3/2013 |
| WO | WO-2013188166 A1 | 12/2013 |

OTHER PUBLICATIONS

Intellectual Property Office, Patents Act 1977: Search Report under Section 17(5), for GB Application No. GB1419263.7, mailed May 28, 2015.
Intellectual Property Office, Patents Act 1977: Search Report under Section 17(5), for GB Application No. GB1408760.5, mailed Dec. 9, 2014.
Intellectual Property Office, Patents Act 1977: Search Report under Section 17(5), for GB Application No. GB140167.1, mailed May 1, 2015.
Silixa, intelligent Distributed Acoustic Sensor (iDAS), Technology Operation Detail Sheet, retreived from internet on Jul. 25, 2016 <http://silixa.com/technology/idas/> pp. 1-4.
Silixa, Ultima (DTS), Technology Operation Detail Sheet, retreived from internet on Jul. 25, 2016 <http://silixa.com/technology/ultima-dts/> pp. 1-3.

* cited by examiner

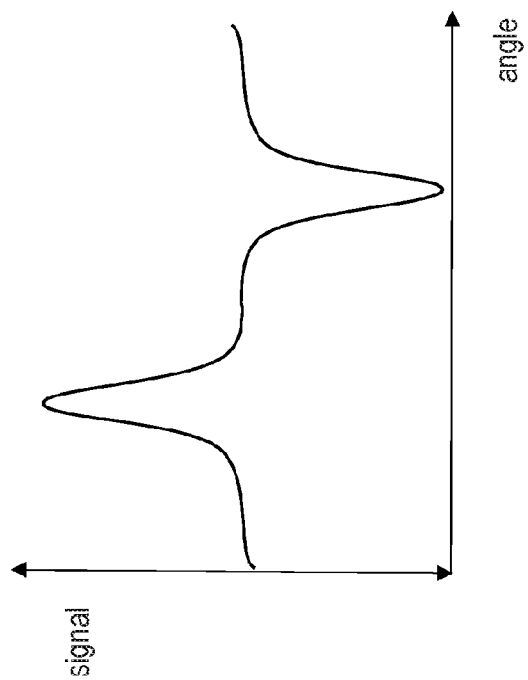
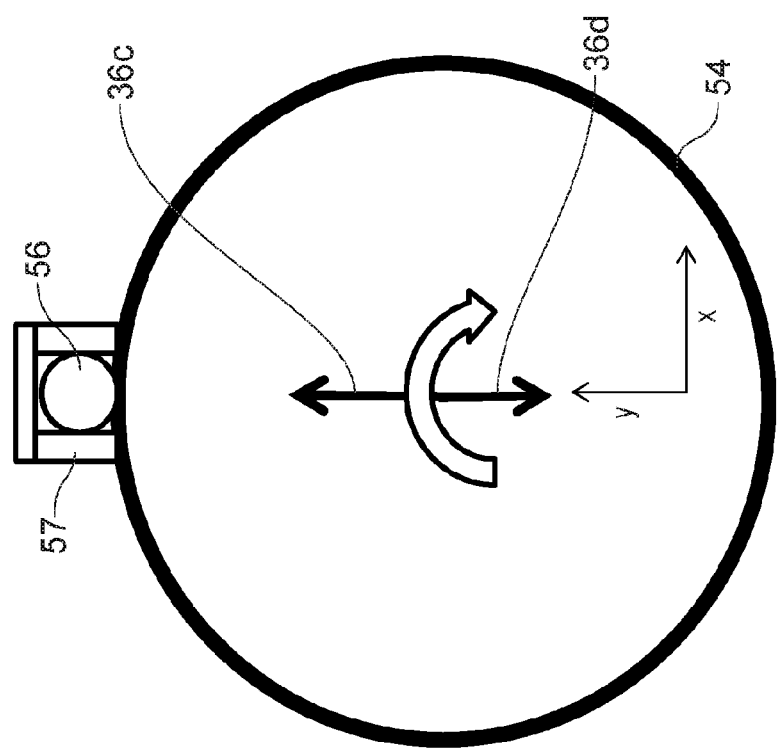
FIG. 8b
FIG. 8a

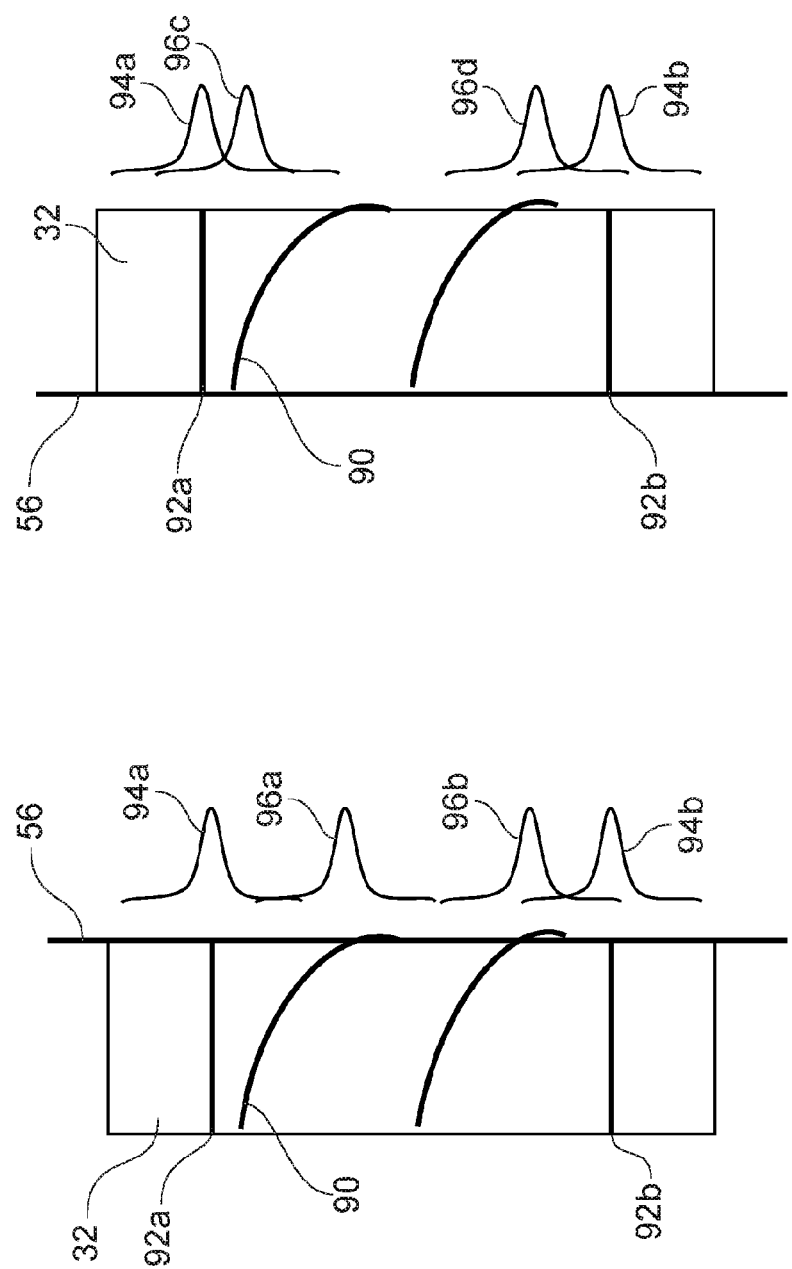

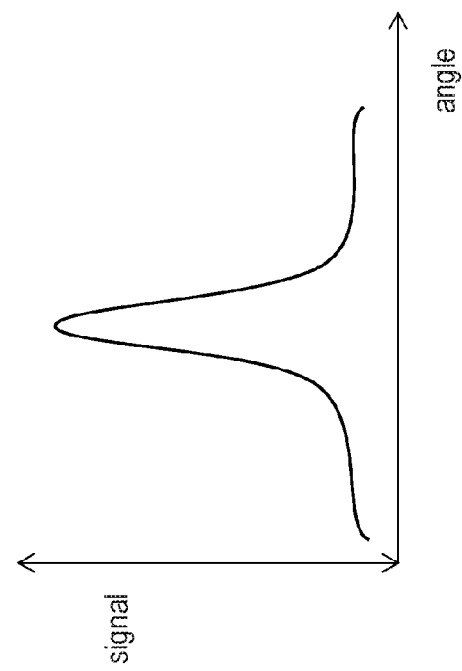
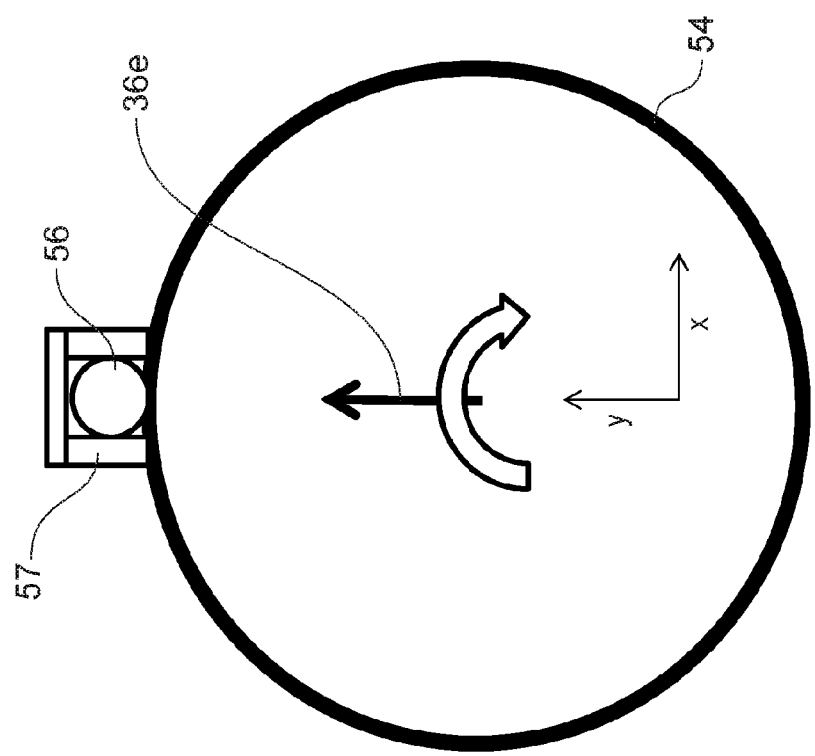
FIG. 10b
FIG. 10a

METHOD AND SYSTEM FOR DETERMINING DOWNHOLE OPTICAL FIBER ORIENTATION AND/OR LOCATION

CROSS-REFERENCE TO RELATED APPLICATIONS

This application claims priority under 35 U.S.C. §371 to Patent Cooperation Treaty Application No. PCT/GB2015/050242, filed Jan. 30, 2015, which claims priority to GB Application No. 1401671.1, filed Jan. 31, 2014, to GB Application No. 1408760.5, filed May 16, 2014, and to GB Application No. 1419263.7, filed Oct. 29, 2014, the entire contents of which are incorporated herein by reference.

TECHNICAL FIELD

The present invention provides a method and system for determining the orientation or location of optical fiber deployed downhole, and particularly optical fiber used for distributed acoustic or temperature sensing. Particular embodiments provide a method and system that ensure that the perforation gun will not damage any optical fibres installed in the well.

BACKGROUND TO THE INVENTION AND PRIOR ART

To detect an acoustic signal downhole, distributed acoustic sensing (DAS) is commonly and effectively used. This method employs fibre optic cables to provide distributed acoustic sensing whereby the fibre optic cable acts as a string of discrete acoustic sensors, and an optoelectronic device measures and processes the returning signal. The operation of such a device is described next.

A pulse of light is sent into the optical fibre, and a small amount of light is naturally back scattered, along the length of the fibre by Rayleigh, Brillouin and Raman scattering mechanisms. The scattered light is captured by the fibre and carried back towards the source where the returning signal is measured against time, allowing measurements in the amplitude, frequency and phase of the scattered light to be determined. If an acoustic wave is incident upon the cable, the glass structure of the optical fibre is caused to contract and expand within the vibro-acoustic field, consequently varying the optical path lengths between the back scattered light scattered from different locations along the fibre The returning signal can be processed in order to measure the acoustical and/or vibrational field(s) at all points along the structure.

In known distributed acoustic sensing systems (DAS), standard fibre optic cables are utilised to obtain a measurement profile from along the entire length of the fibre at intervals ranging from 1-10 meters. Further details regarding the operation of a suitable DAS system, such as the iDAS™, available from Silixa Limited, of Elstree, UK are given in WO2010/0136809. Systems such as these are able to digitally record acoustic fields at every interval location along an optical fibre at frequencies up to 100 kHz. Since the location of the acoustic sensors is known (the fibre deployment being known), the position of any acoustic signal can be thus identified by means of time-of-arrival calculations.

DAS systems find lots of applications in the oil and gas industry, and optical fibers that can be connected to DAS systems, amongst other things, are often installed within wellbores, usually as a metal cable running parallel with the well bore casing clamped to the outside thereof. In a typical oil or gas well, once the well bore has been drilled and the casing installed, cement is used to fill the well bore external of the casing. However, as part of the "completion" process of the well, the casing and cement is perforated within the hydrocarbon bearing regions, to allow hydrocarbons to flow into the casing for extraction. Perforation is typically performed by a perforating gun, which is typically a cylindrical metal tube provided with shaped explosive charges arranged around the circumference thereof. The perforating gun is lowered through the casing to the intended production zone, and the shaped charges are detonated, with the intention of blasting holes through the casing and cement of the well, and into the surrounding rock strata, to allow hydrocarbons to then flow through the created channels into the casing for extraction. Similarly, where a fracturing fluid is to be pumped into the well to fracture the rock strata, the created holes provide routes for the fracturing fluid to exit the well into the surrounding rock.

FIG. 1 illustrates the use of a perforating gun to generate perforations in a well bore casing and cement, and into the surrounding rock strata. Perforating gun 10 comprises a metal cylinder provided with shaped explosive charges arranged around the outer surface thereof. For example, the shaped charges may be provided in lines every 120 degrees around the outer circumference of the gun. The gun is provided with a communications line 12 to the surface for control purposes, to allow the explosive charges to be detonated on command. In use as noted above the gun is lowered to the intended production zone, and the shaped charges detonated to blast through the casing and cement (as shown in FIG. 1(b)), to create production channels in the surrounding rock strata through which oil or gas can flow to enter the well bore (as shown in FIG. 1 (c)).

One issue with the use of perforating guns is to try and prevent the shaped charges from damaging any control or sensing cabling or other lines that may extend along the wellbore external of the casing. For example, optical fibers are commonly installed along the external surface of the casing within the wellbore, either for sensing purposes and/or for control of downhole tools. Care must be taken when using a perforating gun that the shaped charges are not pointed at the external cabling or other lines such that the charges when detonated would sever such lines. As the perforating is performed as part of the well completion, by that point the fibers have typically already been cemented into the well bore, and hence repair can be very costly, or even impossible. To try and prevent such damage occurring, conventionally the fibers and other signalling lines are located between two metal rods or cables, and a magnetometer is provided on the perforating gun to try and detect the metal rods. That is, the rotational orientation of the perforating gun is altered within the casing whilst the magnetometer is used to detect the location of the metal rods either side of the fibers or other cabling. Once the metal rods have been detected, the orientation of the perforating gun can be controlled to ensure that the shaped charges are pointed away from the area of the metal rods, and hence the cabling or other lines to be protected.

One problem with the above arrangement is one of cost, in that the metal rods are usually required to extend along a significant length of the well bore, hence increasing the material and production cost of the well. In addition, the use of magnetometers to detect the rods is not particularly accurate, and particularly in some rock formations or in some regions where magnetic anomalies can occur that interfere with the operation of the magnetometers. Moreover, the presence of the casing and other downhole equipment can interfere with the proper operation of the magnetometers, meaning that it is not reliably possible to rotationally orient the perforating gun within the casing to ensure that the sensor and control lines and/or other cabling will not be damaged by the use of the perforating gun. In addition, the rods also from a potential leakage path up the outside of the casing.

In order to address this problem WO2013/030555 describes a method and apparatus for determining the relative orientation of objects downhole, and especially to determining perforator orientation. The method, illustrated in FIG. 2, involves varying the orientation of an object, such as a perforator gun (302) in the wellbore and activating at least one directional acoustic source (402a-c). Each directional acoustic source is fixed in a predetermined location to the object and transmits an acoustic signal preferentially in a known direction. The directional acoustic source(s) is/are activated so as to generate sound in a plurality of different orientations of said object. An optical fiber (104) deployed down the wellbore is interrogated to provide distributed acoustic sensing in the vicinity of the object and the acoustic signals detected by the optical fiber are analyzed so as to determine the orientation of the at least one directional acoustic source relative to the optical fiber, for instance by looking at the relative intensity in the different orientations. Further details of the operation of the arrangement are described in the document, any and all of which necessary for understanding the present invention being incorporated herein by reference.

Therefore, whilst the arrangement in WO2013/030555 apparently should overcome the cost and inaccuracy of the prior art magnetometer arrangements, the arrangement relies on the operation of a DAS system to detect the directional acoustic sources, with the directional acoustic sources being described as conventional loudspeakers arranged to project sounds forward and located in a casing that absorbs sound emitted in other directions. Conventional loudspeakers typically operate within audible frequency bands, for example in the range 20 Hz to 20 kHz, and a typical DAS of the prior art is usually capable of detecting sound at these frequencies with good spatial resolution. However, the directionality of conventional loudspeakers, even provided in an otherwise insulating casing, is not high, and −3 dB directivity arcs of +/−50 to 60° can be common FIG. 2 has been annotated to show typical example—directivity arcs for the three loudspeakers. As shown, such directivity often means that even if the speaker is pointed away from the optical fibre, the fiber may still pick up a large signal from the speaker. Allowing further for echoes and other multi-path effects within the casing, and the reliability of such a system begins to deteriorate. Basically, using conventional speakers as described in the prior art does not give a high enough directivity for the sound emitted to reliably determine the orientation of the perforating gun.

SUMMARY OF THE INVENTION

In order to address the above problem, alternative mechanisms to locate the optical fiber are necessary, that are more accurate than the conventional audio speaker based method of the prior art. Such mechanisms include a downhole device adapted to be inserted into a wellbore, the downhole device being arranged to contact an interior surface of the well-bore to impart energy to the surface at the contact point, or to detect energy imparted to the surface at the contact point. The downhole device may include a transducer arranged to contact an interior surface of the wellbore to impart energy to the surface at the contact point, wherein the imparted energy may be detected by an optical fiber sensing system comprising the optical fiber to be located. Alternatively, the downhole device may include at least one sensor arranged to contact an interior surface of the wellbore to detect energy imparted to the surface at the contact point, wherein energy has been imparted to an exterior surface of the wellbore by the optical fiber to be located. Both of these solutions to the above noted problem and variations thereof will now be described in more detail.

A first mechanism uses a mechanical tapper arrangement to tap against the inner surface of the casing or tubing, with the position of the tapper rotationally changing so as to tap substantially around the inner circumference of the inner surface. The fiber optic based distributed sensor is operated as a distributed acoustic sensor and records the amplitude of the taps as the tapper rotates so as to tap around the inner circumference of the casing or other tubing. A maxima is then found in the amplitude record of the taps, that should be at the position where the tapper is tapping at a position closest to the optical fiber i.e. the maxima in the amplitude record should indicate the general position of the fiber circumferentially at that position in the casing.

A second mechanism is related, but instead of using a mechanical tapper a heated probe is used that is circumferentially rotated around the inner surface of the casing or other tubing, so as to locally heat the casing the vicinity of the contact point. In this case, the fiber optic distributed acoustic sensor is operated as a distributed temperature sensor, and the local heating of the casing by the heated probed when it is pointing in the direction of the circumferential location of the optical fiber outside the casing or other tubing is detected by the optical fiber as an increase in local temperature. Again, by knowing the rotational position of the heated probe around the inner circumference of the casing or other tubing at the temperature maxima then the position of the optical fiber can be inferred as being at that position.

In one variation of the second mechanism, the transducer may be a probe comprising a heated end adapted to heat the interior surface of the wellbore and a cooled end adapted to cool the interior surface of the wellbore. Here the local heating of the casing by the heated end when it is pointing in the direction of the circumferential location of the optical fiber outside the casing or other tubing, and the local cooling of the casing by the cooled end when it is pointing in the direction of the circumferential location of the optical fiber outside the casing or other tubing is detected by the optical fiber as an increase or decrease in local temperature. By knowing the rotational position of the heated end around the inner circumference of the casing or other tubing at the temperature maxima, or by knowing the rotational position of the cooled end around the inner circumference of the casing or other tubing at a temperature minima, then the position of the optical fiber can be inferred as being at that position.

In a further variation of the second mechanism, the transducer may be a heated probe comprising a helical heater element positioned between first and second heater rings. The heated probe is wrapped around the downhole device in a known relationship such that it is known which part of the probe corresponds to which part of the downhole device. Here the local heating of the casing or other tubing by the helical heater element and the first and second heater rings is detected by the optical fiber as an increase in local temperature to produce at least one temperature maxima. By knowing the relationship between the helical heater element, first and second heater rings, and the downhole device at the at least one temperature maxima, the position of the optical fiber can be inferred without any rotation of the downhole device being required. In both the above mechanisms, therefore, a probe is provided that contacts the inner surface of the casing or other production tubing and imparts energy to the surface at the contact point, whether as, for example, heat energy, or mechanical (vibrational or acoustic) energy. Energy is imparted around the circumference of the casing or other tubing, and a fiber optic distributed sensor located on the outer surface of the casing or other tubing is used to measure and record the energy that it receives whilst the probe is moved to impart energy around the circumference. A record of energy versus position of the probe around the circumference can be obtained, from which maxima in the detected energy measurements can then be found. The position around the circumference which gave the maximum measurement should be the position at which the optical fiber of the fiber optic distributed sensor is located.

In view of the above, from one aspect the present invention provides an apparatus, comprising a downhole device adapted to be inserted into a well-bore, the downhole device including a transducer arranged to contact an interior surface of the well-bore to impart energy to the surface at the contact point.

Another aspect of the invention provides a method of detecting the position of a downhole optical fiber around a wellbore, comprising: deploying a downhole device into the well bore, the downhole device including a transducer arranged to contact an interior surface of the well-bore to impart energy to the surface at the contact point; operating the downhole device within the well-bore; using an optical fiber distributed sensor system to detect the energy imparted to the surface at the contact point; and determining the position of the optical fiber around the well-bore in dependence on the detected energy.

In an alternative mechanism, an optical fiber deployed along the exterior surface of the casing or tubing is arranged to impart energy to the surface of the casing or tubing at the contact point, for example, the optical fiber may be heated so as to impart heat energy. A downhole device deployed inside the casing or tubing and provided with at least one sensor arranged to contact the interior surface of casing or tubing to detect the energy imparted by the optical fiber. In respect of heat energy, the sensor detects the local heating of the casing or tubing in the vicinity of the optical fiber, The at least one sensor on the downhole device may be circumferentially rotated around the inner surface of the casing or other tubing so as to detect one or more maxima in the detected energy as the at least one sensor moves over the interior surface. By knowing the rotational position of the at least one sensor, the position of the optical fiber deployed along the exterior surface of the casing or tubing can be inferred as being at the one or more positions generating the maxima.

In one variation of this mechanism, the at least one sensor is an array of sensors wrapped around the downhole device in a known relationship. The array of sensors are then able to detect one or more maxima in the detected energy at the points of the array that are at or close to the at least one optical fiber. Thus, the position of the optical fiber may be determined from the one or more maxima based on the known relationship between the array of sensors and the downhole device. In this respect, no circumferential rotation of the sensors are needed in order determine the position of the optical fiber In view of the above, a further aspect of the present invention provides an apparatus, comprising a downhole device adapted to be inserted into a well-bore, the downhole device including at least one sensor arranged to contact an interior surface of the wellbore to detect energy from the surface at the contact point. In some embodiments, the at least one sensor may be an array of sensors wrapped around the downhole device in a known relationship such that it is known which part of the array of sensors corresponds to which part of the downhole device.

From a further aspect, the present invention provides a sensor system, comprising a downhole device including at least one sensor arranged to contact an interior surface of the wellbore to detect energy from the surface at the contact point, at least one optical fiber deployed along the exterior surface of the wellbore to impart energy to the interior surface of the wellbore, and a processor coupled to the at least one sensor to detect energy imparted to the interior surface of the wellbore by the at least one optical fiber. In particular, the optical fiber may be heated so as to impart heat energy to the surface of the wellbore.

In further aspects, contact of a transducer with the interior surface of the well-bore is not required. This is particularly the case where the optical fiber distributed sensor is operated as a distributed temperature sensor, which is used to detect a change in heat energy of the well-bore casing, which may result from either local heating or cooling of the casing at discrete points. The heating or cooling may be caused in a contact manner, for example by a heated or cooled probe, or, at least in the case of heating, in a non-contact manner by an energy projection device such as a laser beam, microwave emitter, or the like. The distributed temperature sensor is then able to detect maxima or minima in the temperature profile of the well-bore casing as the probe or beam is swept across the interior surface by the downhole device that carries it, and as a consequence the orientation of the downhole device may be determined.

From a further aspect, therefore, embodiments of the invention also provide an apparatus, comprising: a downhole device adapted to be inserted into a well-bore, the downhole device including a transducer arranged to adapt the heat energy of an interior surface of the well-bore at one or more discrete points so as to alter the temperature of the surface of the well-bore at said one or more discrete points.

In one embodiment the transducer comprises a heated probe adapted to contact the interior surface of the well-bore to impart heat energy to the surface. In another embodiment the transducer may be an energy projection device, such as, for example, a laser.

In one embodiment the transducer is a probe arranged to contact the interior surface of the well-bore, and comprising a heated end adapted to heat the interior surface of the well-bore and a cooled end adapted to cool the interior surface of the well-bore.

In some embodiments the transducer is arranged to move such that the one or more discrete points move over at least a portion of the interior surface of the well-bore. In other embodiments the transducer is further arranged to move such that the one or more discrete points move over at least a portion of the interior surface at a longitudinal position along the wellbore. In further embodiments the transducer is further arranged to move such that the one or more discrete points move over a whole circumference of the interior surface of the wellbore at the longitudinal position.

In some embodiments the heated probe comprises a helical heater element positioned between first and second heater rings, wherein the probe is wrapped around the downhole device in a known relationship such that it is known which part of the probe corresponds to which part of the downhole device.

A further aspect of some embodiments of the invention provides an optical fiber distributed temperature sensor system deployed down a well-bore and adapted to detect the temperature of a surface of the well-bore by an apparatus as described above.

In some embodiments the system is further arranged to detect one or more maxima or minima in the detected temperature as the transducer moves over the interior surface whereby to determine one or more positions of a sensing fiber of the optical fiber distributed sensor system at the one or more positions that give the maxima or minima.

In one embodiment the transducer is a probe comprising a heated end adapted to heat the interior surface of the well-bore and a cooled end adapted to cool the interior surface of the well-bore, and the optical fiber distributed sensor is an optical fiber distributed temperature sensor system.

In one embodiment the system is further arranged to detect one or more minima in the detected temperature as the one or more discrete points move over the interior surface whereby to determine one or more positions of a sensing fiber of the optical fiber distributed sensor system at the one or more positions that give the minima.

In one embodiment the transducer is a heated probe comprising a helical heater element positioned between first and second heater rings, wherein the probe is wrapped around the downhole device in a known relationship such that it is known which part of the probe corresponds to which part of the downhole device, and the optical fiber distributed sensor is an optical fiber distributed temperature sensor system.

In one embodiment the sensor system is further arranged to detect one or more maxima in the detected energy at the points of the heated probe that are at or close to the sensing fiber of the optical fiber distributed temperature sensor system whereby to determine positions of the sensing fiber based on the known relationship between the heated probe and the downhole device.

From a further aspect an embodiment of the invention also provides a method of detecting the position of a downhole optical fiber around a wellbore, comprising: deploying a downhole device into the well bore, the downhole device including a transducer arranged to adapt the heat energy of an interior surface of the well-bore at one or more discrete points so as to alter the temperature of the surface of the well-bore at said one or more discrete points; operating the downhole device within the well-bore; using an optical fiber distributed temperature sensor system to detect the temperature of the surface of the well-bore; and determining the position of the optical fiber around the well-bore in dependence on the detected temperature.

In one embodiment the operating step comprises imparting heat energy to the interior surface around at least a majority of a circumference of the interior surface of the wellbore, and the determining step comprises detecting maxima in the detected temperature measurements and identifying the one or more points at which said maxima occur, wherein the position of the optical fiber can be inferred to be at or close to said points.

Further embodiments of the present invention improve upon the arrangement described in WO2013/030555 by using higher frequency, ultrasonic transducers that are significantly more directional than conventional loudspeakers. Ultrasonic transducers, such as piezo or ferroelectric transducers, are known in the art that generate highly directional soundwaves with frequencies from 100 KHz up to many (50) MHz. As directionality of a sound transducer is proportional to the frequencies emitted therefrom, with higher frequencies typically being more directional, using an ultrasonic transducer results in a significantly more directional output than with conventional loudspeakers. Hence, if the fiber detects the highly directional soundwave, then it becomes possible to be more certain of the orientation of the object to which the transducer is affixed, knowing the relative arrangement between the transducer and the object.

One problem with using such high frequency ultrasonic sources, however, is that a conventional distributed acoustic sensor system can typically only detect sound up to about 100 kHz, and hence will be unable to detect such ultrasound sources. However, in some embodiments of the present invention this problem is solved by operating the DAS equipment in a non-distributed mode, and in particular by operating the laser in the DAS equipment in a continuous wave (cw) mode, such that cw light propagates along the fiber throughout sensing. The fiber is still sensitive to incident ultrasonic vibrations, and the usual backscatter effects (e.g. Rayleigh, Brillouin and Raman) upon which DAS systems rely still occur, but because of the continuous wave operation the sensing equipment is unable to resolve the location of the incident sound along the sensing fiber (there are no pulses being sent along the fiber, the backscatter from which can be timed to determine location). However, the sensing equipment in the DAS is still able to detect that such backscatter effects occur, and hence that there is incident ultrasonic energy incident on the fiber somewhere. From this detection it can then be inferred, absent other sources of incident ultrasonic energy on the fiber, that the ultrasonic source on the perforating gun must be pointing at the fiber, and hence the relative rotational orientation of the fiber and the ultrasonic transducer (and hence the perforating gun) can also be inferred with more accuracy than in the case of the prior art.

The above described operation therefore implies a two stage operation for use of the DAS system in aiding in location and orientation of the perforating gun. Firstly, the DAS system may be operated in normal distributed mode, where sensing pulses are sent down the fiber in a conventional manner, to monitor the deployment of the perforating gun down the casing into the desired production zone. Then, once the position of the perforating gun along the casing has been determined, the DAS system is put into a non-distributed mode of operation, where a continuous signal is sent down the fiber, and backscatter therefrom processed. As noted above, the use of a continuous signal prevents the system processor from resolving spatial location along the fiber, but provided there are no other ultrasonic sources this is not an issue. However, the continuous wave fiber sensor is able to determine that there is an ultrasonic source incident on the fiber. The rotational orientation of the perforating gun is then altered (essentially the gun is rotated within the casing), whilst the ultrasonic source operates, or the rotational orientation is altered and then the source is operated at the new orientation. When the fiber sensor detects the ultrasonic source it means that the source, which is highly directional, must be pointing at the fiber, and hence the rotational orientation of the perforating gun, to which the source is affixed in known relation, can be accurately determined. Having determined the rotational orientation of the perforating gun within the casing, the rotational orientation can then be controlled so that none of the shaped charges in the gun point towards the fiber, or other cabling on the outside of the casing.

In view of the above from a further aspect the present invention provides a method for determining the orientation of a downhole object, comprising: providing the downhole object with a high frequency highly directional sound source fixed in known relation to the object; operating the high frequency directional sound source; rotating the downhole object; and detecting the high frequency directional sound source using an optical fiber acoustic sensing system deployed downhole when the high frequency directional sound source is pointing at the optical fiber; wherein the rotational orientation of the downhole object with respect to the optical fiber is determined based on the detection of the sound source and the known fixed relation between the sound source and the object.

In one embodiment the high frequency directional sound source is an ultrasonic transducer. The ultrasonic transducer may be arranged to operate at frequencies in excess of 50 kHz, or in excess of 100 kHz, or in excess of 200 kHz.

Particularly, in some embodiments the optical fiber sensing system is arranged to operate in a continuous wave mode so as to be able to detect the high frequency sound incident on the optical fiber. In some embodiments this lead to a two stage operation. First the optical fiber acoustic sensing system is operated as a convention distributed acoustic sensor (DAS) system to locate the object downhole, and then operation switches to a second mode, where the optical fiber acoustic sensing system operates in a continuous wave mode to determine the rotational orientation of the object at the located position.

Further features and aspects of the invention will be apparent from the appended claims.

BRIEF DESCRIPTION OF DRAWINGS

Embodiments of the present invention, presented by way of example only, will now be described, with reference to the accompanying drawings, wherein like reference numerals refer to like parts, and wherein:

FIGS. 8a and 8b are drawings illustrating the operation and effect of a third type of transduced in the form of a probe with a varying temperature profile used as a third embodiment of the present invention;

FIGS. 9a and 9b are drawings illustrating the operation and effect of a fourth type of transducer used as a forth embodiment of the present invention, wherein the transducer utilises a helical heater element;

FIGS. 10a and 10b are drawings illustrating the operation and effect of an array of sensors on the perforated gun used as a fifth embodiment of the present invention;

DETAILED DESCRIPTION OF PREFERRED EMBODIMENTS

In an embodiment of the invention a perforating gun 32 is provided. The perforating gun 32 comprises a generally cylindrical object having sections provided therein in which shaped explosive charges 38 can be mounted. Suitable detonators (not shown) and control electronics (not shown) are also included, controlled via control line 34. In use, as known in the art, the perforating gun is lowered into the casing of a wellbore during the completion phase, and moved into the intended production zone. The shaped charges are then fired to blow holes through the casing and cement into the surrounding rock strata.

In order to allow the rotational orientation of the perforating gun to be determined when the gun is deployed within the wellbore casing, a transducer 36 is provided. The form of the transducer 36 differs between embodiments, as will be described. For example, in a first embodiment the transducer comprises a mechanical tapper that taps against the inner surface of the casing or other tubing within which the perforating gun travels. In a second embodiment, however, the transducer is a heated probe that locally heats the internal surface of the casing or other tubing. The fiber optic distributed sensor is operated as a distributed temperature sensor, as is known in the art, and detects the local heating of the casing in the vicinity of the optical fiber when the heated probe is rotationally pointing towards the position of the fiber on the outside of the casing or other tubing.

Figure 1:
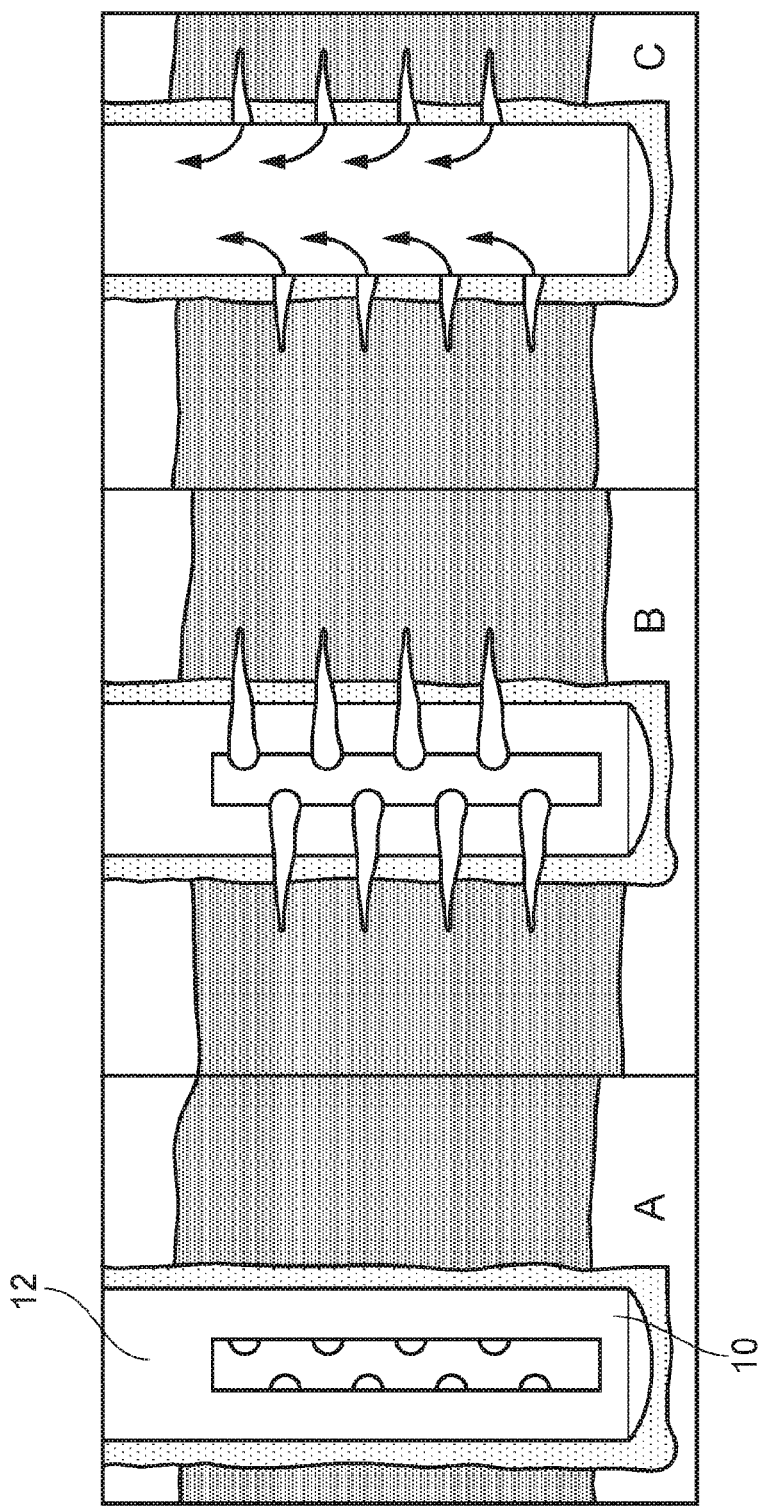
FIG. 1 is a drawing illustrating the prior art operation of a perforating gun.
Figure 2:
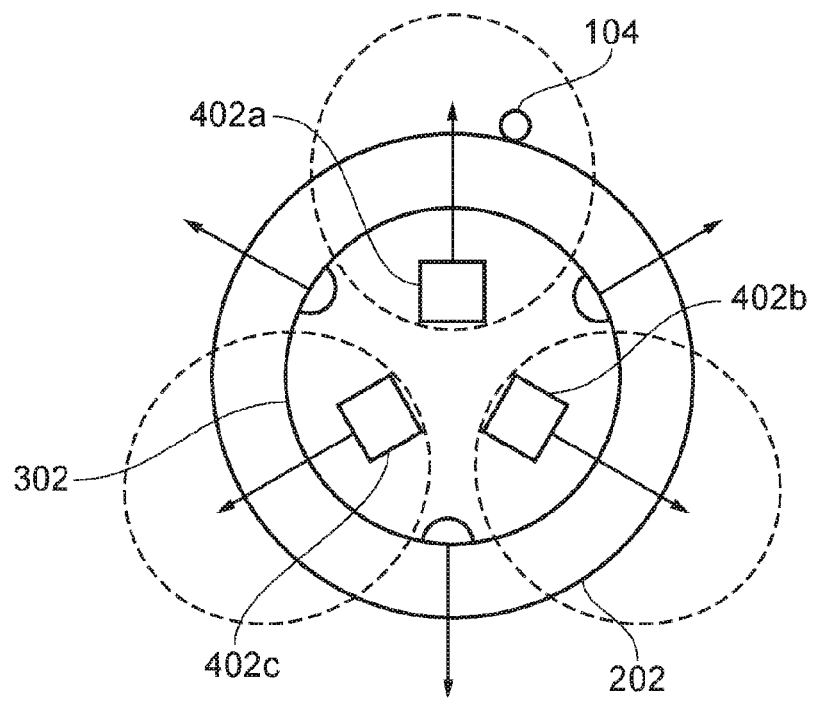
FIG. 2 is a drawing from the prior art illustrating the wide-field effects of loud speakers of the prior art.
Figure 3:
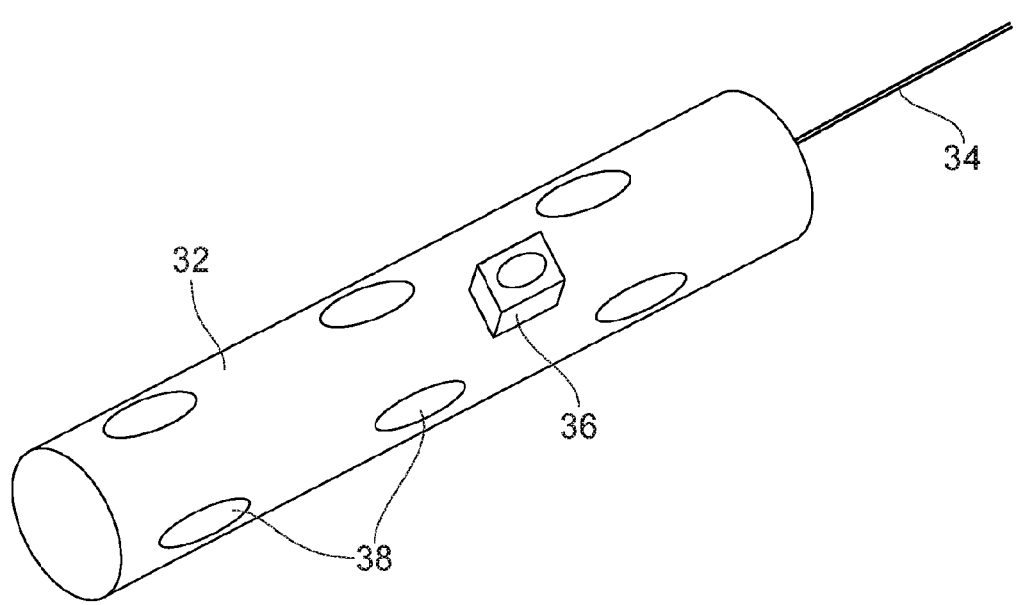
FIG. 3 is a drawing of a perforating gun of an embodiment of the present invention, provided with at least one transducer thereon.

Within FIG. 3 a single transducer is shown. However, in other embodiments multiple transducers may be included, for example arranged around the circumference of the perforating gun. For example, the transducers 36 may be equiangularly arranged around the circumference. In addition or alternatively, plural (e.g. two or more) transducers may be located at the same rotational position on the perforating gun.

Figure 5:
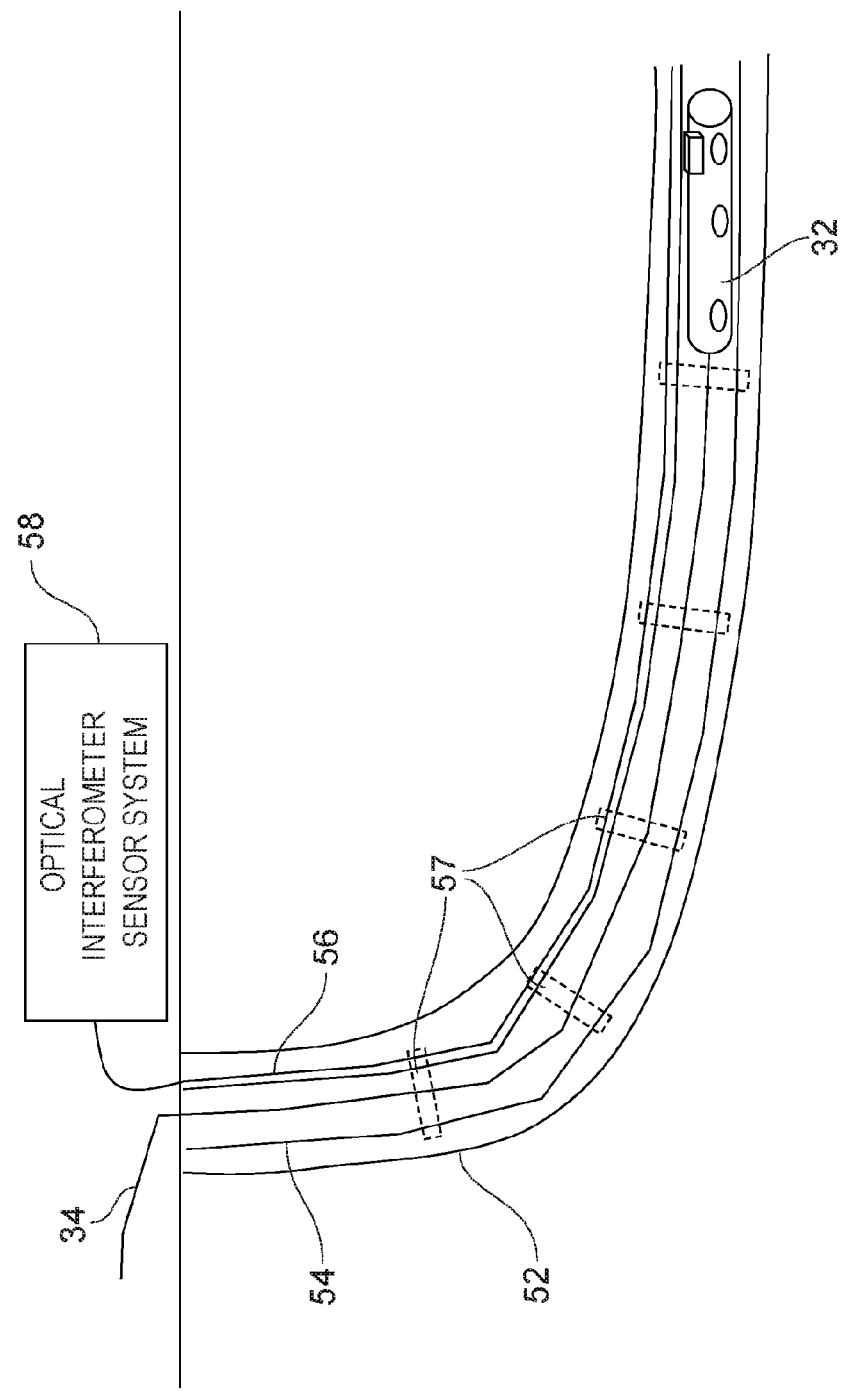
FIG. 5 is a diagram illustrating a typical deployment scenario for embodiments of the present invention.

FIG. 5 illustrates a typical deployment scenario for embodiments of the present invention. Here, a wellbore 52 has been drilled, and casing 54 installed therein, cement surrounding the casing to secure the casing within the wellbore 52. The casing is provided running along its outer surface with one or more optical fibers 56 or other cabling, for signalling, sensing or control purposes. The cabling 56 including the optical fiber is secured to the casing 54 via clamps 57, located typically every few meters along the casing. During completion of the wellbore perforating gun 32 is inserted into the casing 54, and moved along the casing 32 to the intended production zone of the well. An optical interferometric sensing system 58, which in one embodiment is a distributed acoustic sensing (DAS) system, is provided, connected to optical fiber 56. The sensing system 58 may operate in a distributed acoustic sensing mode as known in the art to monitor the insertion of the perforating gun 32 into and along the casing 54. The DAS system may be a Silixa® iDAS™ system, the details of operation of which are available at the URL http://www.silixa.com/technology/idas/, and which is also described in our earlier patent application WO2010/0136809, any details of which that are necessary for understanding the present invention being incorporated herein by reference. Alternatively, when required to be a temperature sensor, as required by one of the embodiments to be described below, then the optical interferometric sensing system 58 may be a Silixa® Ultima™ distributed temperature sensor, available from Silixa Limited, of Elstree, UK, and described at http://www.silixa.com/technology/dts/.

Figure 4B:
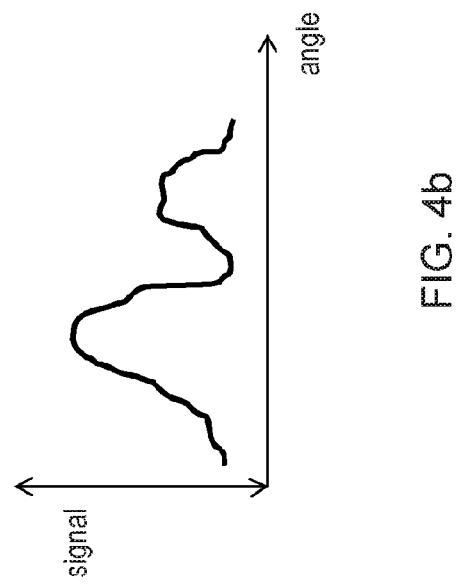
FIGS. 4a and 4b are drawings illustrating the operation and effects of a first type of transducer in the form of a mechanical tapper, used as a first embodiment of the present invention.

A first embodiment of the present invention will be described with respect to FIGS. 4a and 4b.

Figure 4A:
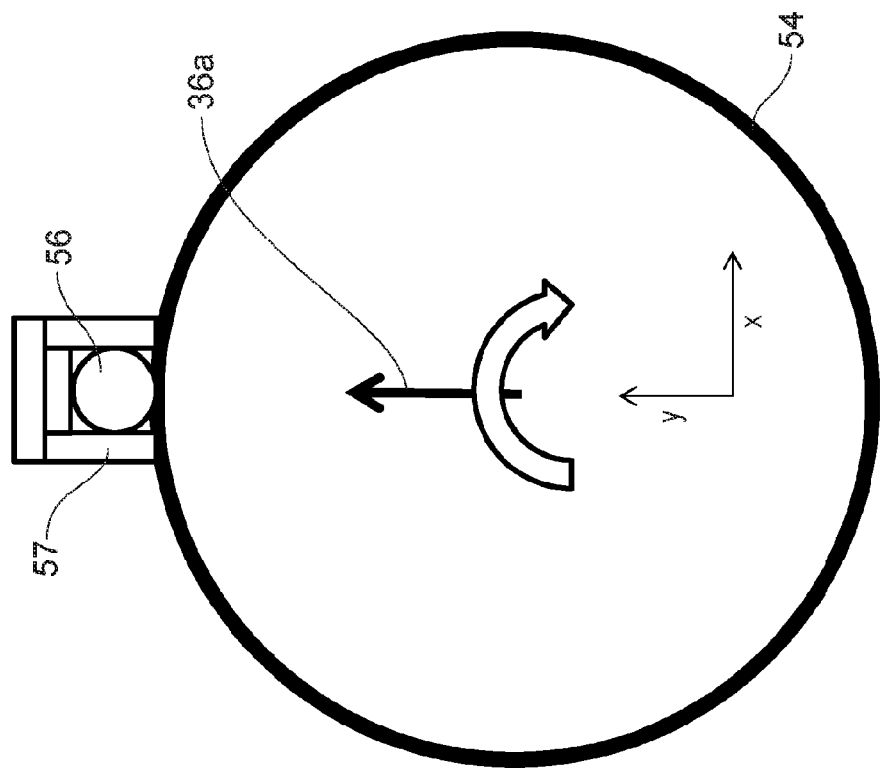

FIG. 4a illustrates that the transducer 36 may be an electrical or mechanical tapper device 36a, that is arranged to rotate about an axis and tap at discrete points on the inner surface of casing 54 as it rotates through 360 degrees. In this embodiment the optical interferometric sensing system 58 operates as a distributed acoustic sensor (DAS), which listens to the acoustic energy from the taps and determines its amplitude and/or power. A plot of the measured amplitude and/or power with respect to angular position of the tapper as it rotates within the casing is made, as shown in FIG. 4b. With reference to the orientational axes shown in FIG. 4a, a minima in the measured amplitude or power plot is expected when the tapper is aligned with the x-axis of FIG. 4a i.e. when it is substantially orthogonal to the position of the optic fiber 56, whilst a primary maxima in amplitude or power is obtained when the tapper 36a is tapping directly at the fiber 56. In addition, a secondary maxima in the measured signal is obtained when the tapper 36a is tapping directly away from the fiber, i.e. when it is tapping in an opposite direction 180 degrees away from the position of the fiber. That is, with respect to the axes shown on FIG. 4a, minima in the detected signal occur when the tapper is pointing in the + or −x directions, whilst a primary (largest) maxima is obtained when the tapper is pointing directly towards the fiber 56, (i.e. in the +y direction) and a secondary (smaller) maxima is obtained when the tapper is pointing directly away from the fiber (i.e. in the −y direction).

Regarding the clamp 57 that clamps the fiber 56 to the casing, in this embodiment it is preferable (although not essential) that the clamp contains a flexible filler material to permit the fiber to have a greater freedom of movement in the +/−y directions, to permit the fiber to be more responsive to the vibrational energy of the tapper when the tapper is pointed directly toward the fiber.

A second embodiment of the invention will now be described with respect to FIGS. 6a and 6b. In this embodiment the optical interferometric sensing system 58 operates as a distributed temperature sensor (DTS) that acts to determine the temperature of the casing 54, inter alia. The transducer 36 is a heated probe, similar to the tip of a soldering iron, that is rotationally mounted on the perforating gun, or alternatively on another down-hole device that acts as a carriage for the probe. In some embodiments this may be preferable, so that the heated tip is not maintained near the explosives that are contained within the perforating gun. The heated probe is in contact with the inner surface of the casing 54, and acts to heat the casing wall in the immediate vicinity of the probe. The degree of local heating provided by the probe need not be large, and may even be less than 1K, for the reason that modern DTS systems have very high temperature resolutions, as high as 0.01K.

Figure 6B:
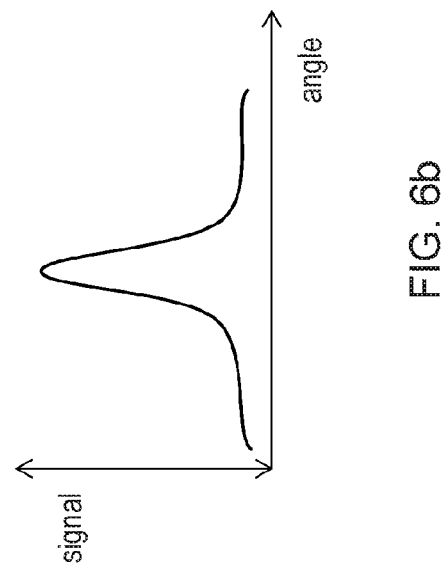
FIGS. 6a and 6b are drawings illustrating the operation and effects of a second type of transducer in the form of a heated probe used as a second embodiment of the present invention.
Figure 6A:
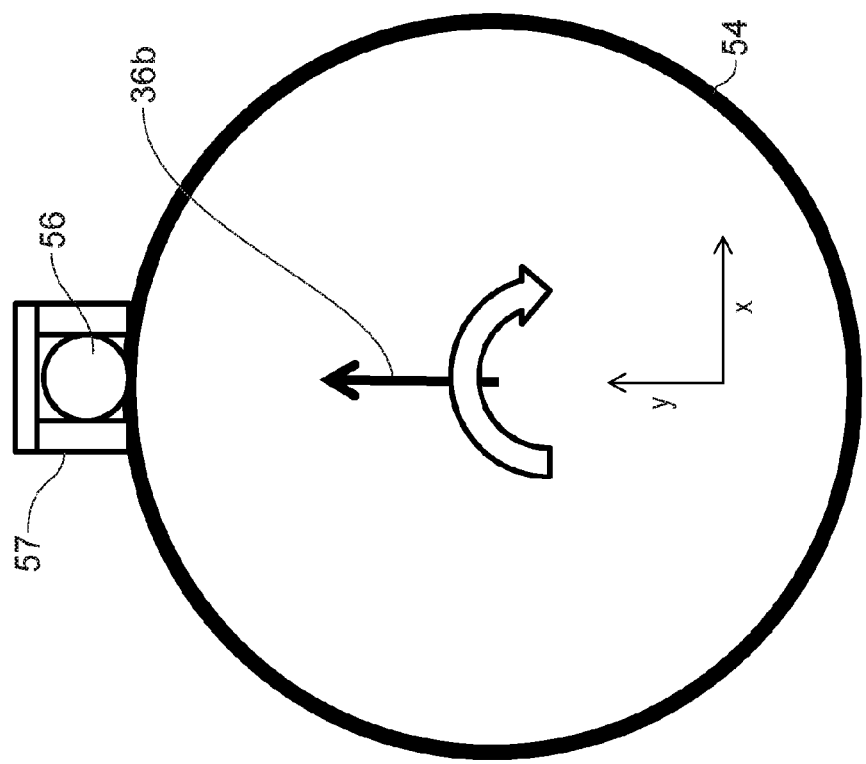

The local heating of the casing wall in the immediate vicinity of the heated probe 36b is detected by the optical fiber, which forms part of the DTS system, and the DTS system is able to plot measured temperature against the rotational position of the heated probe 36b, to give a typical plot as shown in FIG. 6b. From FIG. 6b it can be seen that a single maxima is obtained in the temperature plot against rotational angle of the probe at the point where the probe is pointing directly towards the optical fiber i.e. the heated tip of the probe is closest to the optical fiber. By detecting this maxima in the temperature plot the angular position of the optical fiber around the casing 54 can be inferred. That is, with reference to the axes shown in FIG. 4a, a single maxima is obtained when the probe is pointed in the +y direction i.e. directly at the fiber.

With respect to the clamp 57 that clamps the fiber to the casing, a conventional clamp may be used; there are no special considerations for the clamp in this embodiment.

Figure 7:
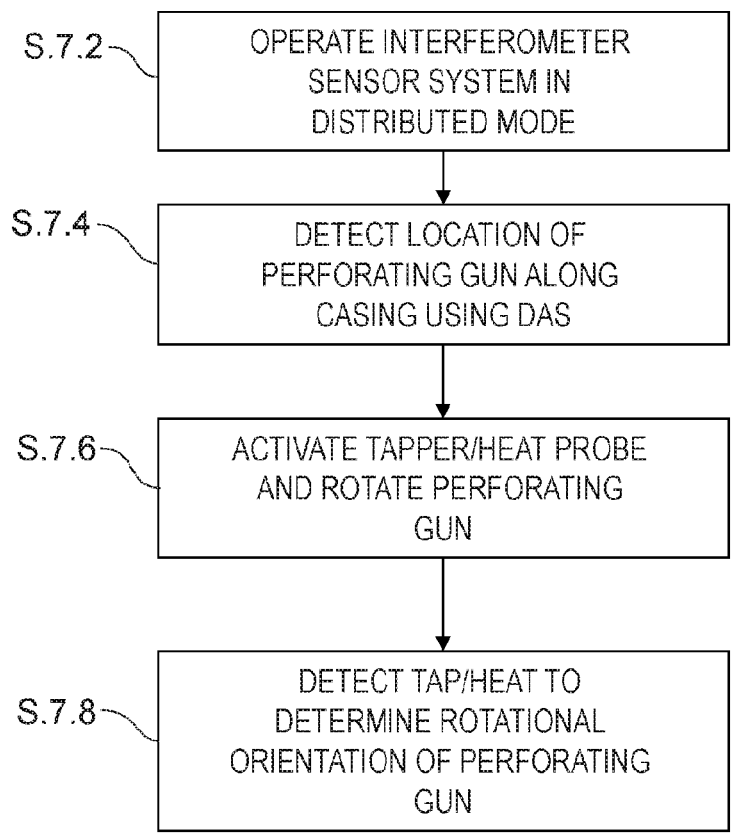
FIG. 7 is a flow diagram illustrating the typical steps employed in an embodiment of the invention.

FIG. 7 is a flow diagram illustrating the sequence of operations in the described embodiments, given the equipment described above. In particular, at s.7.2 the interferometer sensor system is first operated in conventional distributed acoustic sensing mode, whilst the perforating gun 32 is inserted into the casing. In this way the DAS can the track the location of the perforating gun at step 7.4, as the gun is moved along the casing into the desired production zone of the well that is to be perforated.

Once the location of the gun within the well casing has been determined, and the gun located where required, then at step 7.6 the tapper or heat probe are activated and the perforating gun (or other downhole carrier device on which they are mounted) is rotated through 360 degrees (or through any angle required to detect the fiber) whilst the optical fiber sensing system (i.e. DAS or DTS, as appropriate) records its detection output. Once the tapper or heat probe have been activated against the inner wall of the casing or other tubing through a sufficient arc to detect the fiber, the plot of measurements made by the DAS or DTS system can then be examined to determine any maxima therein, and thereby infer the angular (or rotational) position of the fiber around the casing at that point along the casing, as previously described. This determination is performed at step 7.8, as shown.

A third embodiment of the invention will now be described with respect to FIGS. 8a and 8b. In this embodiment the optical interferometric sensing system 58 operates as a distributed temperature sensor (DTS) that acts to determine the temperature of the casing 54, inter alia. The transducer 36 is a probe with a heated tip 36c and a cooled tip 36d, wherein the probe is heated on one side and cooled on the opposite side, that is rotationally mounted on a perforating gun, or alternatively on another down-hole device that acts as a carriage for the probe. In some embodiments this may be preferable, so that the heated part of the probe is not maintained near the explosives that are contained within the perforating gun. The probe is in contact with the inner surface of the casing 54, and acts to heat or cool the casing wall in the immediate vicinity of the probe. The degree of local heating provided by the probe need not be large, and may even be less than 1K, for the reason that modern DTS systems have very high temperature resolutions, as high as 0.01K.

The local heating or cooling of the casing wall in the immediate vicinity of the probe is detected by the optical fiber 56, which forms part of the DTS system, and the DTS system is able to plot measured temperature against the rotational position of the probe, to give a typical plot as shown in FIG. 8*b*. From FIG. 8*b* it can be seen that a single maxima is obtained in the temperature plot against rotational angle of the probe at the point where the probe is pointing directly towards the optical fiber i.e. the heated tip 36*c* of the probe is closest to the optical fiber. Additionally, a single minima is obtained in the temperature plot against rotational angle of the probe at the point where the probe is pointing directly away from the optical fiber, i.e. the cooled tip 36*d* of the probe is pointing directly towards the optical fibre and the heated tip 36*c* of the probe is pointing directly away from the optical fiber. That is, with reference to the axes shown in FIG. 8*a*, a single maxima is obtained when the heated tip 36*c* of the probe is pointed in the +y direction i.e. directly at the fiber, and a single minima is obtained when the cooled tip 36*d* of the probe is pointed in the +y direction, i.e. directly at the fiber, and the heated tip 36*c* of the probe is pointed in the −y direction, i.e. directly away from the fiber. Consequently, no rotation is needed in order to tell whether the probe is pointing in a general direction towards the fiber, where there will be local heating of the casing wall, or in a general direction away from the fiber, where there will be a local cooling of the casing wall. Furthermore, by detecting this maxima or minima in the temperature plot the angular position of the optical fiber around the casing 54 can be inferred. In this respect, fewer rotation positions need to be measured in order to locate the cable position accurately.

A fourth embodiment of the invention will now be described with respect to FIGS. 9*a* and 9*b*. In this embodiment the optical interferometric sensing system 58 operates as a distributed temperature sensor (DTS) that acts to determine the temperature of the casing 54, inter alia. The transducer in this embodiment is a heated probe comprising a helical heater element 90 wrapped around a perforating gun 32 (or other downhole carrier device), and two heater rings 92*a-b* positioned at either end of the helical heater element 90. The helical heater element 90 and heater rings 92*a-b* are installed on the gun 32 in a predetermined configuration. That is to say, the probe is installed on the gun 32 in a known orientation such that it is known which parts of the helical heater element 90 and heater rings 92*a-b* correspond to which parts of the gun 32, and furthermore it is known how the helical heater element 90 is positioned with respect to the heater rings 92*a-b*. The helical heater element 90 and heater rings 92*a-b* are in contact with the inner surface of the casing 54, and act to heat the wall of the casing 54 in the immediate vicinity. The degree of local heating provided by the probe need not be large, and may even be less than 1K, for the reason that modern DTS systems have very high temperature resolutions, as high as 0.01K.

The local heating of the casing wall in the immediate vicinity of the probe is detected by the optical fiber 56, which forms part of the DTS system, and the DTS system is able to plot measured temperature against the position of the probe. In the temperature plot, temperature peaks will be produced at the points where the heater rings 92*a-b* and helical heater element 90 are in contact with the parts of the casing 54 to which the optical fiber 56 is attached, that is, the points at which the probe is positioned closest to the optical fiber 56. In more detail, there will be two peaks at fixed positions produced in the location of the heater rings 92*a-b*, and at least one peak produced from the helical heater element 90, depending on the number of helical windings.

Generally, however, there will be at least as many peaks indicating the presence of a helical winding as there are complete helical windings. For example, the helical heater element 90 may comprise two and a half complete helical windings wrapped around the perforating gun 32. In one situation, the gun 32 may be orientated such that the optical fiber 56 is located above the two full helical windings and the half of helical winding, in which case three peaks in the temperature plot will be generated. In another situation, the gun 32 may be orientated such that the optical fiber 56 is located above the two full helical windings only, in which case only two peaks will be generated in the temperature plot.

Based on the known relationship between the positions of the helical element 90 and the heater rings 92*a-b*, the distance between the helical element peak(s) and the heater ring peaks can be used to determine which portion of the helical element 90 is causing the temperature peak(s). Therefore, since the configuration of the helical heater element 90 on the gun 32 is also known, it is known which part of the gun 32 is closest to the optical fiber 56 and thus the orientation of the gun 32 inside the casing 54 can be inferred from this information.

For example, in FIG. 9*a* it is shown that the optical fiber 56 is located to one side of the gun 32. The heater rings 92*a-b* produce temperature peaks 94*a-b* respectively, identifying the top and bottom of the perforated gun 32 within the casing 54, wherein the longitudinal position of the heater ring peaks 94*a-b* along the length of the gun 32 will be the same regardless of where the fiber 56 is located, as illustrated by FIG. 9*b*. As such the heater ring peaks 94*a-b* act as reference points for temperature peaks 96*a-b* produced by the helical heater element 90, as will be described below. Furthermore, by identifying where along the length of the optical fiber 56 the heater rings 92*a-b* are located, the location of the gun 32 along the length of the casing may also be inferred.

As stated previously, the relationship between the positioning of helical heater element 90 with respect to the position of the heater rings 92*a-b* is known. Therefore, the relative distances between the heater ring peaks 94*a-b* and the helical heater element peaks 96*a-b* can be measured and compared with the known relationship to determine which parts of the helical heater element 90 have produced the temperature peaks 96*a-b*. As the position of the optical fiber 56 with respect to the gun 32 varies, for example, as shown in FIG. 9*b*, the position of the helical heater element peaks 96*c-d* with respect to the heater ring peaks 94*a-b* varies in dependence on the location of the optical fiber 56, the distance between the helical heater element peaks 96*c-d* and the heater ring peaks 94*a-b* being used to determine which part of the helical heater element 90 is causing the local heating of the casing wall. As a result, no rotation of the probe or the gun 32 is required in order to determine the location of the optical fiber 56 around the probe or the gun 32.

A fifth embodiment of the invention will now be described with respect to FIGS. 10*a* and 10*b*. In this embodiment the transducer is at least one temperature probe installed on a perforating gun (or other downhole carrier device). For example, the transducer is an array of sensors installed on the perforating gun (or other downhole carrier device) in a predetermined configuration. The one or more optical fibers 56 running along the side of the casing 54 are heated, and may optionally form part of a heat-pulse system. The local heating of the casing wall by the optical fiber 56 is detected by the array of sensors arranged in the known configuration over the perforation gun 32. The array of sensors is able to detect the temperature around the circumference of the casing 54 wall and then feed the temperature data back to some external processing means located at the surface via the control line 34 of the perforating gun 32. The external processing means is able to determine which of the sensors provides the highest temperature reading, wherein the sensor with the highest value is located nearest the fiber, the position of the fiber being determined based on the known position of the sensor. Consequently, there is no need to rotate the perforating gun 32 to determine the location of the optical fiber.

Alternatively, as shown in FIG. 10*a*, a single probe 36*e* is rotationally mounted on the perforating gun 32 and acts as a single temperature sensor coupled to the control line 34 of the perforating gun 32. The local heating of the casing 54 wall by the optical fiber 56 is detected by the probe 36*e*, and the external processing means coupled to the control line 34 is able to plot measured temperature against the rotational angle of the probe 36*e*, to give a typical plot as shown in FIG. 10*b*. From FIG. 10*b* it can be seen that a single maxima is obtained in the temperature plot against rotational angle of the probe at the point where the probe is pointing directly towards the optical fiber i.e. the probe 36*e* is closest to the heated optical fiber. That is, with reference to the axes shown in FIG. 10*a*, a single maxima is obtained when the probe is pointed in the +y direction i.e. directly at the fiber. By detecting this maxima in the temperature plot the angular position of the optical fiber around the casing 54 can be inferred.

A further embodiment will now be described with respect to FIGS. 11 to 15.

In order to allow the rotational orientation of the perforating gun to be determine when the gun is deployed within the wellbore casing, an ultrasonic transducer 36, such as piezo or ferroelectric transducer, is provided. The transducer operates at any ultrasonic frequency, although preferably from 100 kHz to 50 MHz, with the directionality of the ultrasonic signal being dependent on the frequency and the transducer design. The precise design of the ultrasonic transducer is beyond the scope of the present application, suffice to say that many highly directional ultrasonic transducer designs are known in the art suitable for use in the present embodiment.

Ultrasonic transducers can be obtained, for example, from Olympus NDT Corporation, of Waltham, Mass., USA, or from components suppliers such as Premier Farnell, or RS. For example, the PROWAVE 235AC130 TRANSMITTER, ULTRASONIC, 235 KHZ, 13 MM, available from Premier Farnell UK Limited, of Leeds, UK, provides a −6 dB beamwidth of only 15 degrees at 235 kHz.

Figure 11:
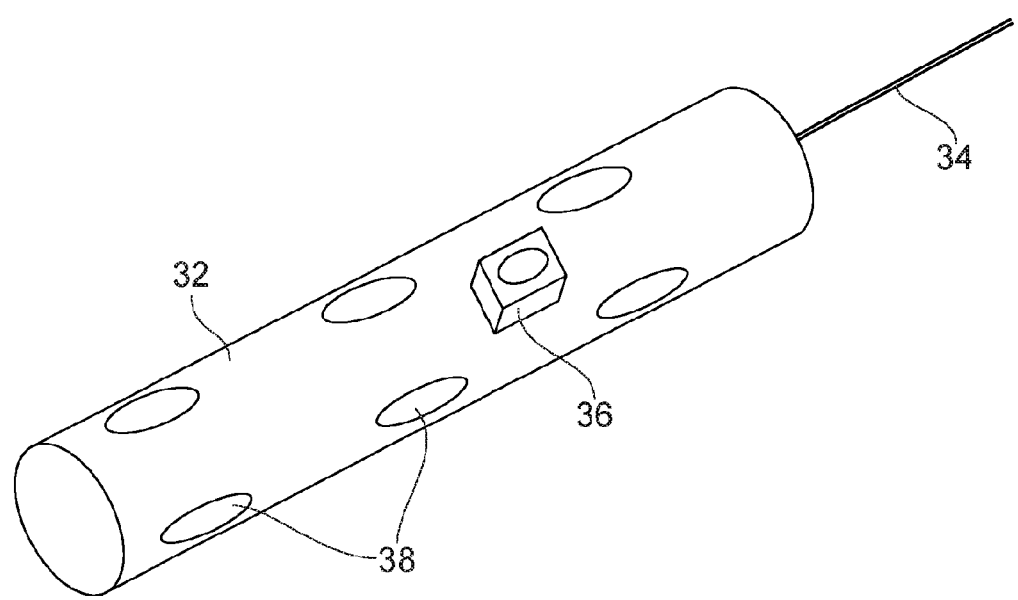
FIG. 11 is a drawing of a perforating gun of an embodiment of the present invention, provided with at least one ultrasonic source thereon.
Figure 12:
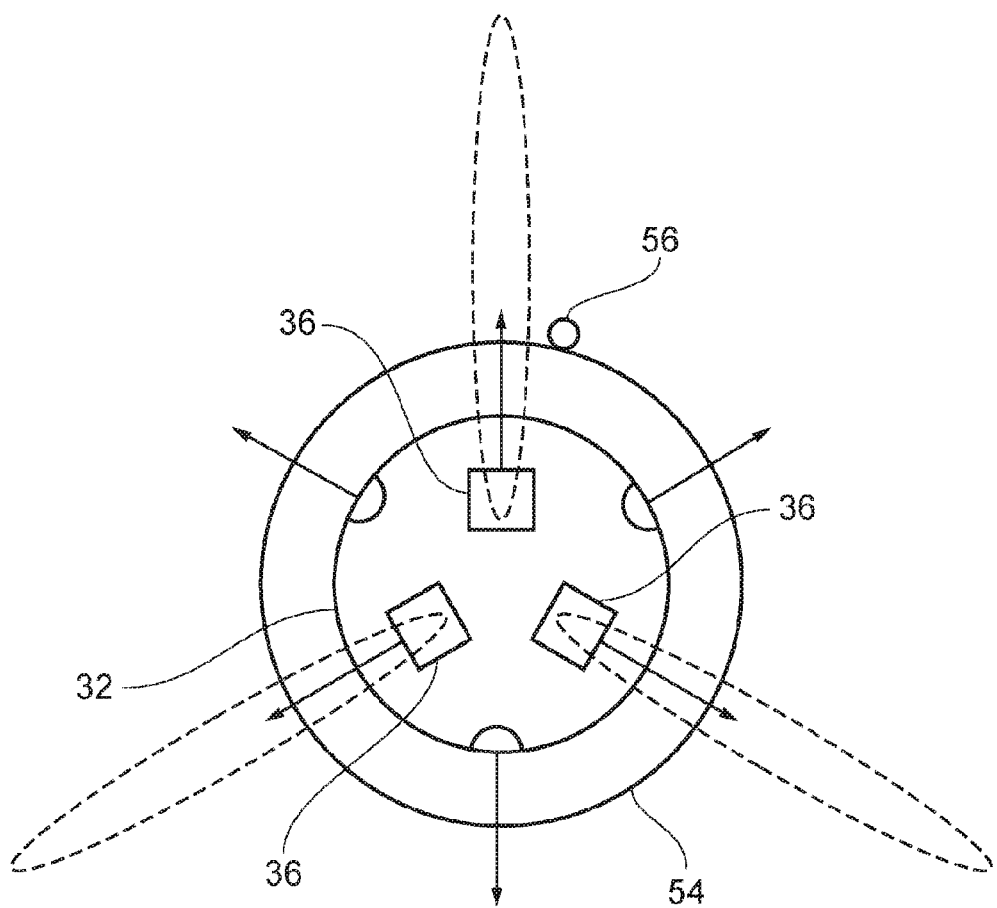
FIG. 12 is a drawing of a perforating gun of an embodiment of the present invention illustrating the narrow-field effects of the use of an ultrasonic source.

Within FIG. 11 a single ultrasonic transducer is shown. However, in other embodiments multiple ultrasonic transducers may be included, for example arranged around the circumference of the perforating gun as shown in FIG. 12. Here the arrangement is such that the transducers 36 are equiangularly arranged around the circumference. In addition or alternatively, plural (e.g. two or more) ultrasonic transducers may be located at the same rotational position on the perforating gun (not shown in FIG. 12). Where plural transducers are provided arranged around the circumference of the gun, then the transducers may operate on the same frequency, provided the beamwidths are narrow enough so as not to significantly overlap. For example, provided the −6 dB beamwidths of rotationally adjacent transducers do not overlap, then there should be sufficient separation. In FIG. 12, the dotted lines illustrate example soundfields from the transducers. As shown, the sound beamwidths are very narrow, thus providing greater accuracy in determining the rotational orientation of the gun.

However, in other more preferable embodiments, the transducers 36 arranged at different positions around the circumference of the gun operate on different frequencies. Providing different known frequencies from transducers at known relative positions can help the acoustic sensing system resolve the rotational orientation of the perforating gun within the casing more accurately.

Where there are plural (two or more) transducers located side by side at the same angular position on the circumference of the gun then these transducers should operate at different frequencies. In such a case the different frequencies would be picked up by the fiber optic acoustic sensor simultaneously, when the plural transducers are commonly directed at the fiber. The different frequencies can act as both an identification and rotational position signature for the perforating gun, and provide a measure of anti-jamming performance, for example in the presence of an inadvertent interfering signal. For example, the side-by-side transducers may operate at two known ultrasonic frequencies, which may be widely separated in the spectrum, for example by 50 kHz or more. In use the fiber optic acoustic sensor would pick up both signals simultaneously, at the same rotational position of the gun. If the rotational position that provides the maximum value for both signals is found, then it is highly likely that the gun is in a position where the transducers are pointing directly at the fiber, and the incident ultrasound on the fiber is as a result of a direct path from the transducers to the fiber, rather than having suffered any reflections or multi-path propagation between the transducers and the fiber. In such a case, the ability of the arrangement to accurately determine the rotational position of gun with respect to the fiber is increased.

Figure 13:
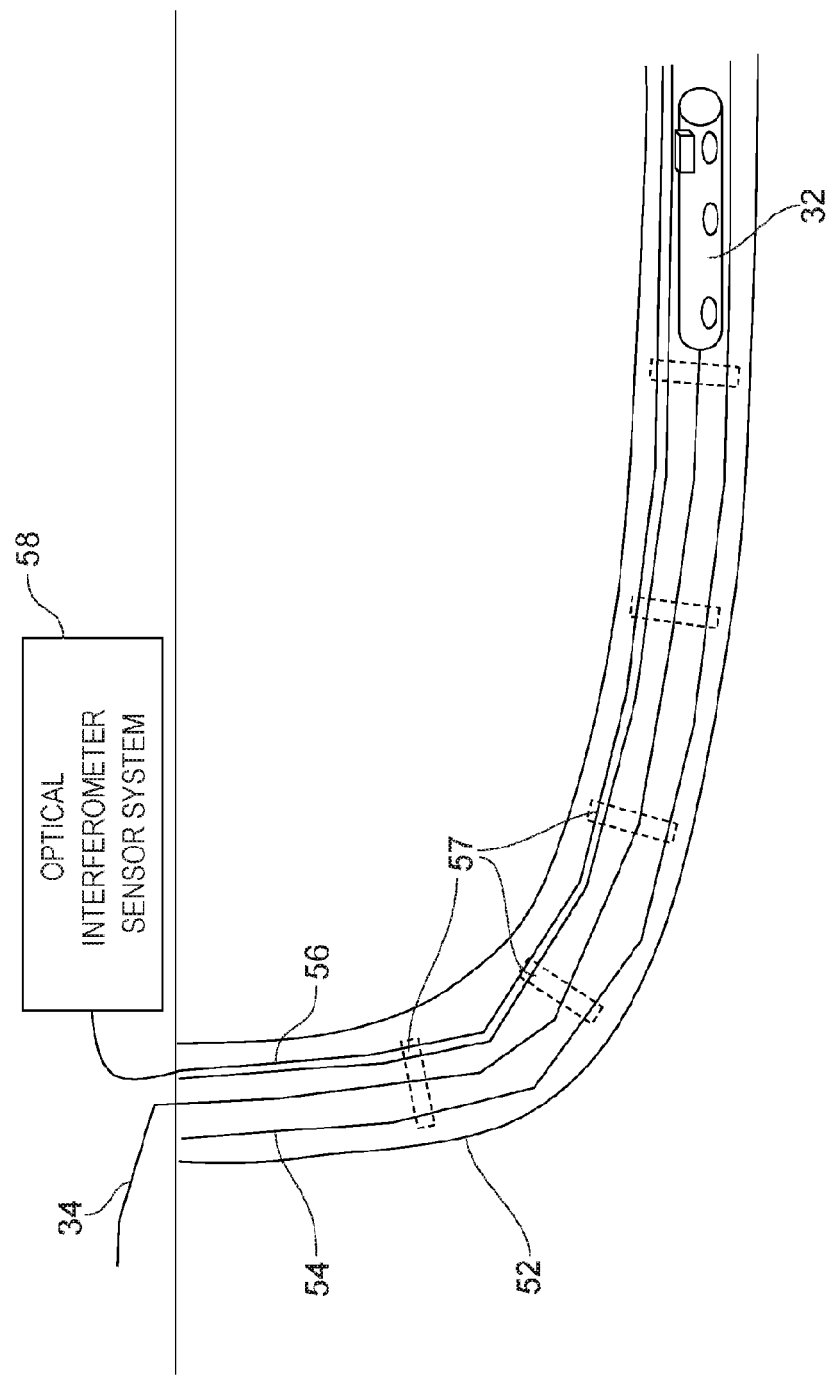
FIG. 13 is a diagram illustrating a typical deployment scenario for embodiments of the present invention.

FIG. 13 illustrates a typical deployment scenario for embodiments of the present invention. Here, a wellbore 52 has been drilled, and casing 54 installed therein, cement surrounding the casing to secure the casing within the wellbore 52. The casing is provided running along its outer surface with one or more optical fibers 56 or other cabling, for signalling, sensing or control purposes. The cabling 56 including the optical fiber is secured to the casing 54 via clamps 57, located typically every few meters along the casing. During completion of the wellbore perforating gun 32 is inserted into the casing 54, and moved along the casing 32 to the intended production zone of the well. An optical interferometric sensing system 58, such as a distributed acoustic sensing (DAS) system is provided, connected to optical fiber 56, which may operate in a distributed acoustic sensing mode as known in the art to monitor the insertion of the perforating gun 32 into and along the casing 54. The DAS system may be a Silixa™ iDAS™ system, the details of operation of which are available at the URL http://www.silixa.com/technology/idas/, and which is also described in our earlier patent application WO2010/0136809, any details of which that are necessary for understanding the present invention being incorporated herein by reference.

In the present embodiment the sensing system 58 may operate in a distributed acoustic sensing mode to monitor the insertion of the perforating gun 32 into the casing 54, and to determine the position of the gun 32 along the casing.

However, the sensing system 58 may then be switched to operate in a continuous wave mode, which is used to determine the rotational orientation of the gun within the casing. In the continuous wave mode, the laser of the sensing system is operated in a continuous wave mode to continually send laser light along the fiber during the sensing periods. The fiber is affected by incident ultrasonic sound waves from the ultrasonic transducers in the same manner as known in the art i.e. Rayleigh, Brillouin, and Raman backscatter occur, dependent on the incident sound energy, but due to the continuous wave propagating in the fiber rather than pulses, any timing information, which is indicative of location along the fiber is lost. Therefore, the continuous wave backscatter from the incident ultrasonic wave can be detected and resolved by the interferometer detector unit in the interferometric sensing system 58 to detect the ultrasonic incident sound energy on the fiber, but not to locate it along the fiber—it is simply possible to tell that such ultrasonic sound energy is incident on the fiber somewhere along its length.

Figure 14:
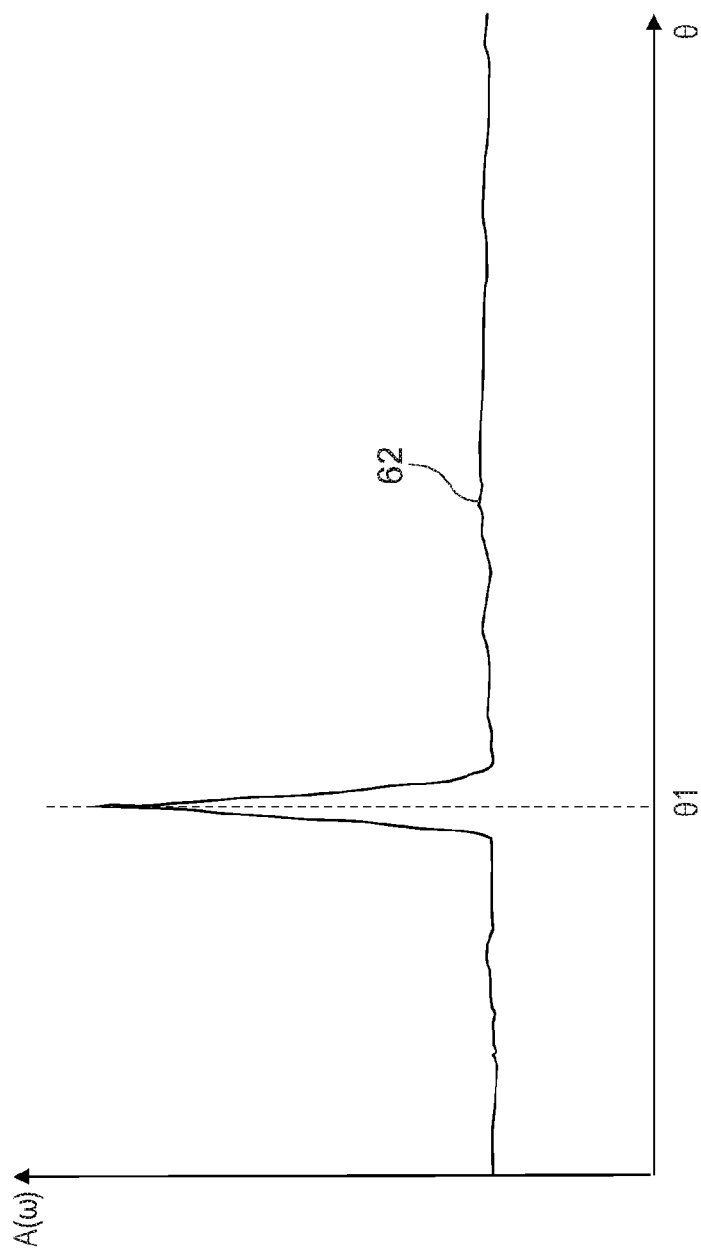
FIG. 14 is a graph illustrating the detection output of the continuous wave interferometer sensor system, with respect to rotational angle of the perforating gun.

The advantage of the continuous wave operation, however, is that because there is no need to take into account pulse timing of pulses propagating along the fiber in the detector to determine location, the detector is able to detect much higher frequency sound incident on the fiber than is the case than when operating in distributed (DAS) mode, and in particular should be able to detect incident ultrasound across the ultrasound frequency band. Hence, in the present embodiment, with the sensor system 58 operating in continuous mode, any ultrasound being emitted by source 36 on the perforating gun will be detected by the sensor system 58 as the arc of emitted ultrasound sweeps over the fiber as the perforating gun is caused to rotate in the casing. FIG. 14 illustrates an example output plot of the amplitude of sound at ultrasound frequency ω (which may be in the range e.g. 100 kHz to 50 MHz) with respect to rotational angle θ of the perforating gun 32 within the casing 54, as detected by sensor system 58 operating in continuous wave mode. As will be seen, as the gun 32 rotates within the casing the output amplitude A(ω) at frequency ω remains substantially constant at a background level, until the source 36 is pointing at the fiber at rotational position $\theta_1$. At that rotational position the ultrasonic source 36 is pointing directly at the fiber, and this manifests itself as a spike in the detected sound on the fiber at frequency ω of the ultrasonic source. Hence, at that point the operator knows that ultrasonic source 36 is pointing directly at the fiber, and by then knowing the position of the source 36 on the perforating gun 32, the rotational orientation of the perforating gun is thus found.

Figure 15:
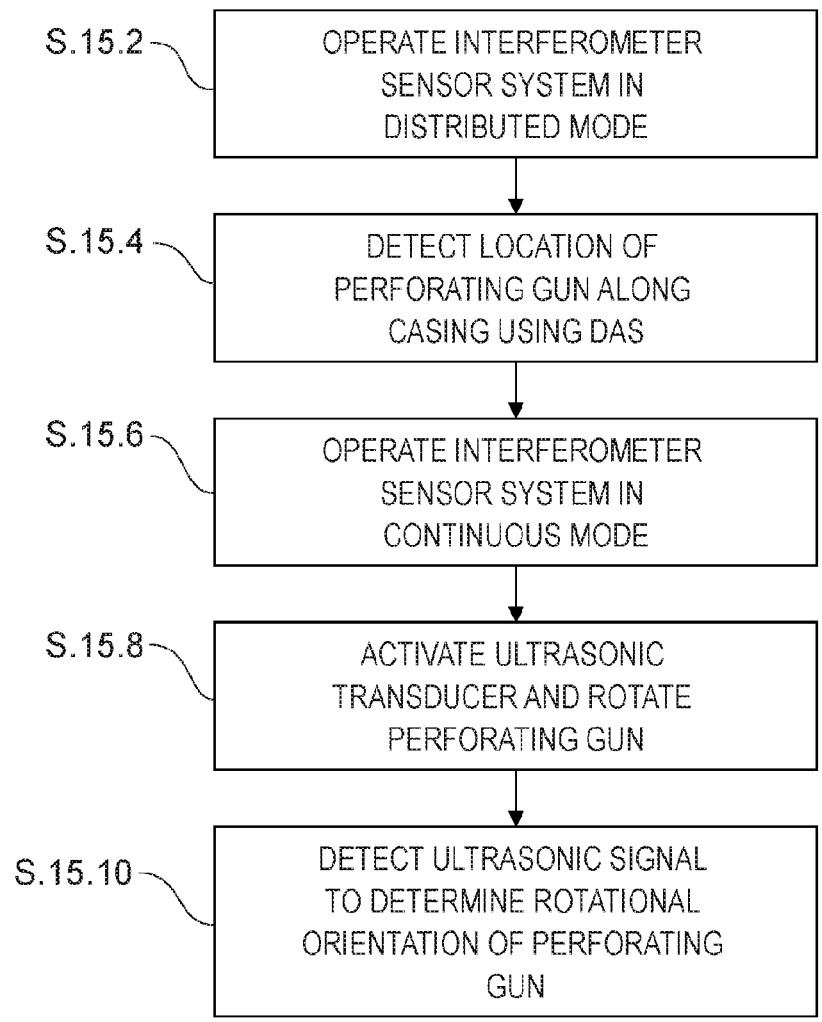
FIG. 15 is a flow diagram illustrating the typical steps employed in an embodiment of the invention.

FIG. 15 is a flow diagram illustrating the sequence of operations in the present embodiment, given the equipment described above. In particular, at s.15.2 the interferometer sensor system is first operated in conventional distributed acoustic sensing mode, whilst the perforating gun 32 is inserted into the casing. In this way the DAS can the track the location of the perforating gun at step 15.4, as the gun is moved along the casing into the desired production zone of the well that is to be perforated.

Once the location of the gun within the well casing has been determined, and the gun located where required, the interferometer sensing system 58 is then switched into continuous wave mode operation, at s.15.6. As described above, this prevents the sensor form determining position of incident sound along the fibre, but allows the sensor to detect incident sound of much higher frequency that is incident anywhere along the fiber. With the sensing system 58 operating in this mode, the one or more ultrasonic transducers 36 provided on the perforating gun 34 are turned on, and caused to emit a highly directional ultrasound beam. The perforating gun is then rotated in the casing, such that the ultrasound beam sweeps around as the gun rotates (s.15.8). When the gun is rotated such that ultrasound source is pointing at the fiber 56 the ultrasound beam sweeps over the fiber, thus causing backscatter effects in the fiber, which are detected by the interferometric sensor system 58, thus manifesting themselves as a peak in the sensor output, as described. When the peak is detected the operator then knows that at the point the perforating gun is oriented such that the ultrasound source is pointing at the fiber, and hence given a priori knowledge of the location and orientation of the source on the gun, the rotational orientation of the gun within the casing is found.

In one preferred embodiment, the acoustic source 36 is located so that its beam is not located on the same radial axis as the axes of fire of any of the shaped charges 38. In such an embodiment, when the acoustic source beam is pointing at the fiber, and the high frequency sound therefrom is being detected as incident on the fiber, the operator thus knows that at that point none of the shaped charges are pointing at the fiber, and hence it is safe to fire the charges.

Various modifications may be made to the above described embodiments, to provide further embodiments. For example, whilst in the second embodiment above we mention that the heat probe may be carried on a different down-hole device than the perforating gun, such modification also applies to the first embodiment. That is, in further embodiments instead of being carried on the perforating gun the transducer, whether it be a tapper or heat probe, is instead carried on another downhole device, for example a dedicated downhole pig, or other wireline or slickline downhole tool whose purpose is to mount and transport the transducer. In such a case embodiments of the invention are used to locate the optical fiber external to the casing, and any perforating gun that follows the pig or other downhole tool is then aimed independently, given the obtained knowledge of the location of the fiber from the embodiments of the invention.

As another variant embodiment, based on the second embodiment described above, instead of using a heated probe to impart heat energy to the interior wall of the casing, instead a high power semiconductor diode laser is used instead. That is, a high power laser diode is carried by a downhole tool, and once in situ may be activated to direct a high power (e.g. >~1 W) substantially collimated beam at the interior wall, so as to heat the wall at the point of incidence. The laser diode may then be rotated, or the downhole tool on which it is mounted rotated, so as to slowly sweep the laser beam around the interior circumference of the casing at the longitudinal position along the casing to be measured. An example high power laser diode is, for example, the TO-220 laser diode, available from OSRAM Opto Semiconductors GmbH of Wernerwerkstrasse 2, D-93049 Regensburg, Federal Republic of Germany. Other similar laser diodes are also available, that may be suitable for downhole applications, and in particular be able to operate at relatively high ambient temperatures encountered downhole.

As noted, the laser beam incident on the interior wall of the casing heats the wall at the point of incidence, and the increased energy can be detected by the optical fiber distributed temperature sensor in the same manner as described previously with respect to the second embodiment. That is, as the laser sweeps around the interior circumference of the wall, the DTS measures the temperature of the casing during the sweep to determine a temperature profile with respect to sweep angle, and the angular position at which a maxima is present should correspond to the position of the fiber around the casing, at that longitudinal measurement position. In this respect, the obtained temperature profile with respect to laser sweep angle should be similar to that of FIG. 6b, with a single maxima at the angular position of the fiber on the exterior of the casing. This position is determined by the DTS, and output to the user, as described previously in respect of the second embodiment.

With this variant on the second embodiment, therefore, a non-contact arrangement is provided, where there is no contact required on the interior wall of the casing. Instead, directional electromagnetic energy, in this instance in the form of a laser, is directed at the interior wall of the casing, in order to heat it up.

In this respect therefore, the wavelength of the laser may be any that provides a suitably collimated beam so as to be able to heat a discrete spot on the interior surface of the casing. For example, the wavelength of the laser may extend from the infra-red downwards, provided suitably small devices are available that can be deployed downhole at reasonable cost.

Various further modifications to the above described embodiment may be made, whether by way of addition, deletion, or substitution, to provide further embodiments, any and all of which are intended to be encompassed by the appended claims.

What is claimed is:

1. An apparatus, comprising:
   i) a downhole device adapted to be inserted into a wellbore, the downhole device including a transducer arranged to adapt the heat energy of an interior surface of the wellbore at one or more discrete points so as to alter a temperature of the surface of the wellbore at said one or more discrete points, wherein the transducer is further arranged in use to adapt the heat energy to the interior surface of the wellbore around at least a majority of a circumference of the interior surface of the wellbore; and
   ii) an optical fiber distributed temperature sensor system having a sensing optical fiber deployed down the wellbore, the optical fiber distributed temperature sensor system being adapted to detect the change in temperature of a surface of the wellbore caused by the downhole device contained within the wellbore, wherein the detection of the change in temperature comprises detecting maxima or minima in the detected temperature measurements and identifying the one or more points at which said maxima or minima occur, wherein a position of the optical fiber around the wellbore can be inferred to be at or close to said points.

2. The apparatus according to claim 1, wherein the transducer comprises a heated probe adapted to contact the interior surface of the wellbore to impart heat energy to the surface.

3. The apparatus according to claim 2, wherein the heated probe comprises a helical heater element positioned between first and second heater rings, wherein the probe is wrapped around the downhole device in a known relationship such that it is known which part of the probe corresponds to which part of the downhole device.

4. The apparatus according to claim 1, wherein the transducer is a probe arranged to contact the interior surface of the wellbore, and comprising a heated end adapted to heat the interior surface of the wellbore and a cooled end adapted to cool the interior surface of the wellbore.

5. The apparatus according to claim 1, wherein the downhole device is a transporter pig, perforating gun, or other wireline or slickline downhole device on which the transducer may be carried.

6. The apparatus according to claim 1, wherein the transducer is arranged to move such that the one or more discrete points move over at least a portion of the interior surface of the wellbore.

7. The apparatus according to claim 6, wherein the transducer is further arranged to move such that the one or more discrete points move over at least a portion of the interior surface at a longitudinal position along the wellbore.

8. The apparatus according to claim 7, wherein the transducer is further arranged to move such that the one or more discrete points move over a whole circumference of the interior surface of the wellbore at the longitudinal position.

9. The apparatus according to claim 1, wherein the optical fiber distributed temperature sensor system is further arranged to detect one or more maxima or minima in the detected temperature whereby to determine one or more relative positions of the sensing optical fiber of the optical fiber distributed sensor system with respect to the orientation of the downhole device.

10. The apparatus according to claim 9, wherein the transducer is a probe comprising a heated end adapted to heat the interior surface of the wellbore, the heated end being arranged to move over the interior surface of the wellbore.

11. The apparatus according to claim 10, wherein the optical fiber distributed temperature sensor system is further arranged to detect one or more maxima in the detected temperature as the one or more discrete points move over the interior surface whereby to determine one or more positions of a sensing fiber of the optical fiber distributed temperature sensor system at the one or more positions that give the maxima.

12. The apparatus according to claim 1, wherein the transducer is a heated probe comprising a helical heater element positioned between first and second heater rings, wherein the probe is wrapped around the downhole device in a known relationship such that it is known which part of the probe corresponds to which part of the downhole device.

13. The apparatus according to claim 12, wherein the optical fiber distributed temperature sensor system is further arranged to detect one or more maxima in the detected energy at the points of the heated probe that are at or close to the sensing fiber of the optical fiber distributed temperature sensor system whereby to determine positions of the sensing fiber based on the known relationship between the heated probe and the downhole device.

14. The apparatus according to claim 1, the transducer comprising an electromagnetic energy projection device arranged to direct electromagnetic energy at an interior surface of the wellbore to impart energy to the surface at an incident point.

15. The apparatus according to claim 14, wherein the electromagnetic energy projection device is a laser.

16. The apparatus according to claim 14, wherein the electromagnetic energy is collimated and heats the interior surface of the wellbore at the incident point above the ambient temperature.

17. The apparatus according to claim 14, wherein the electromagnetic energy projection device is arranged to sweep over at least a portion, and preferably a whole circumference, of the interior surface of the wellbore so as to heat the interior surface above the ambient temperature around the swept arc.

18. A method of detecting the position of a downhole optical fiber around a wellbore, comprising:
deploying a downhole device into the wellbore, the downhole device including a transducer arranged to adapt the heat energy of an interior surface of the wellbore at one or more discrete points so as to alter the temperature of the surface of the wellbore at said one or more discrete points;
operating the downhole device within the wellbore;
using an optical fiber distributed temperature sensor system to detect the temperature of the surface of the wellbore; and
determining the position of the optical fiber around the wellbore in dependence on the detected temperature,
wherein the operating step comprises adapting the heat energy of the interior surface around at least a majority of a circumference of the interior surface of the wellbore, and the determining step comprises detecting maxima or minima in the detected temperature measurements and identifying the one or more points at which said maxima or minima occur, wherein the position of the optical fiber can be inferred to be at or close to said points.

* * * * *